(12) United States Patent
Shentu et al.

(10) Patent No.: US 9,238,648 B2
(45) Date of Patent: Jan. 19, 2016

(54) ASYMMETRIC SYNTHESIS METHOD, RELATED RAW MATERIAL AND PREPARATION METHOD OF (S,S)-2,8-DIAZABICYCLO[4,3,0]NONANE

(71) Applicant: SHANGHAI PUYI CHEMICAL TECHNOLOGY CO., LTD, Shanghai (CN)

(72) Inventors: Xiaobo Shentu, Shanghai (CN); Yantao Qi, Shanghai (CN); Lingshi Xie, Shanghai (CN); Bo Wang, Shanghai (CN)

(*) Notice: Subject to any disclaimer, the term of this patent is extended or adjusted under 35 U.S.C. 154(b) by 0 days.

(21) Appl. No.: 13/977,526

(22) PCT Filed: Sep. 20, 2012

(86) PCT No.: PCT/CN2012/081699
§ 371 (c)(1),
(2) Date: Jun. 28, 2013

(87) PCT Pub. No.: WO2013/053281
PCT Pub. Date: Apr. 18, 2013

(65) Prior Publication Data
US 2014/0066626 A1    Mar. 6, 2014

(30) Foreign Application Priority Data
Oct. 14, 2011 (CN) .......................... 2011 1 0312411

(51) Int. Cl.
| C07D 207/00 | (2006.01) |
| C07D 471/04 | (2006.01) |
| C07D 207/24 | (2006.01) |
| C07D 207/14 | (2006.01) |
| C07D 207/27 | (2006.01) |

(52) U.S. Cl.
CPC ............ *C07D 471/04* (2013.01); *C07D 207/14* (2013.01); *C07D 207/24* (2013.01); *C07D 207/27* (2013.01); *Y02P 20/55* (2015.11)

(58) Field of Classification Search
None
See application file for complete search history.

(56) References Cited

U.S. PATENT DOCUMENTS 4,299,768 A    11/1981  Labaz
5,770,597 A *   6/1998  Kim et al. .................. 514/230.2

FOREIGN PATENT DOCUMENTS

JP    11012278 A    *  7/2007
WO   WO 02/096426 A1 * 12/2002

OTHER PUBLICATIONS

Rovis, T. et al. Scope of the Asymmetric Intramolecular Stetter Reaction Catalyzed by Chiral Nucleophilic Triazolinylidene Carbenes. J. Org. Chem. 2008, vol. 73, p. 2038.*
Kocienski, PJ. Protecting Groups. THIEME. 2005, p. 188.*

*Primary Examiner* — Rita Desai
*Assistant Examiner* — Ben S Michelson
(74) *Attorney, Agent, or Firm* — Avery N. Goldstein; Blue Filament Law

(57) ABSTRACT

The present invention relates to an asymmetric synthesis method of a chiral intermediate (S,S)-2,8-diazabicyclo[4,3,0]nonane (I) of moxifloxacin, wherein an imide or enamine compound is obtained by dehydration reaction of the pyrrolidine-3-ketone as shown in formula (II) and chiral amine(R)-1-phenylethylamine, followed by the reduction of the imide or enamine compound to obtain a compound of formula (III) or (IV) having the chiral structure of formula (I), and then a compound of formula (I) is obtained by intramolecular cyclization, and removal of the chiral auxiliary group and amino-protecting group. The present invention also relates to pyrrolidine-3-ketone as shown in formula (II) and a preparation method therefor,

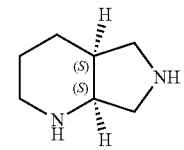

(I)

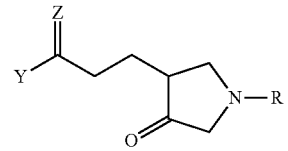

(II)

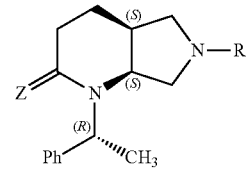

(III)

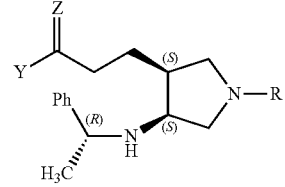

(IV)

and in the formula (I), (II), (III), (IV), R is an amino-protecting group, especially $C_{1-4}$ alkoxycarbonyl, benzyloxycarbonyl or benzyl which can be removed by hydrolysis or hydrogenation. $Z=H_2$ or O; when $Z=H_2$, Y is chlorine, bromine, iodine, methanesulfonate, tosylate, hydroxyl or hydroxyl with protection; and when $Z=O$, Y is $OR_1$, and $R_1$ is $C_{1-4}$ alkyl.

3 Claims, No Drawings

ASYMMETRIC SYNTHESIS METHOD, RELATED RAW MATERIAL AND PREPARATION METHOD OF (S,S)-2,8-DIAZABICYCLO[4,3,0]NONANE

FIELD OF TECHNOLOGY

The present invention relates to the technical field of preparation for a medicine intermediate, and in particular relates to the technical field of preparation for a chiral intermediate of quinolone antibacterial moxifloxacin, specifically an asymmetric synthesis method of a chiral intermediate (S,S)-2,8-diazabicyclo[4,3,0]nonane of quinolone antibacterial moxifloxacin, and simultaneously, the present invention further relates to a raw material pyrrolidine-3-ketone compound for preparing the intermediate and a preparation method therefor.

DESCRIPTION OF RELATED ARTS

As a third-generation quinolones broad-spectrum antibiotic, moxifloxacin has been widely used for clinical treatment of respiratory tract infections since 1999, such as acquired pneumonia, acute exacerbation of chronic bronchitis, acute bacterial sinusitis, etc.

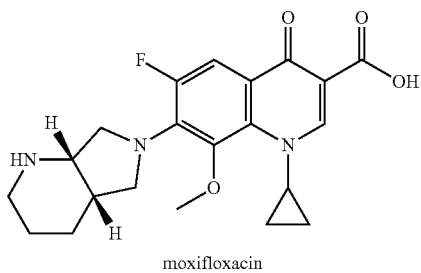 [SMILES: COc1c(N2C[C@@H]3CCCN[C@@H]3C2)c(F)cc2c(=O)c(C(=O)O)cn(C3CC3)c12]

moxifloxacin (S,S)-2,8-diazabicyclo[4,3,0]nonane (I) is a key chiral intermediate of moxifloxacin and its molecular structure consists of two skeleton structures, i.e. piperidine and pyrrolidine, and two chiral centers, and the preparation methods that have been reported are mainly classified as two synthesis routes: piperidine route and pyrrolidine route (route 1).

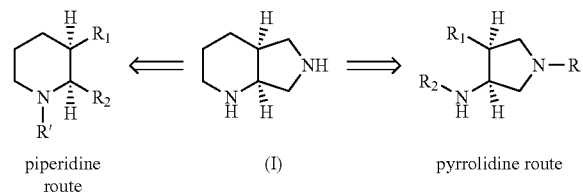

Route 1

As for piperidine route, plenty of synthesis methods have been reported and also become the processes that are employed in the current industrial production, all these processes involve use of 3,4-dipicolinic acid as starting material as well as high-pressure hydrogenation of pyridine, reduction of carboxylic acid carbonyl and other reactions, there are high requirements on equipment in high-pressure hydrogenation and expensive reducing agents in reduction of carboxylic acid carbonyl, and the processes of this route all involve chiral resolution and need to solve the problem of racemic recycling of wasted isomer in resolution process and the problem of recovery and reuse of resolving agents, in addition, they are complex in process flows and are neither economical nor environment-friendly.

Disclosed in the U.S. Pat. No. 5,703,244 is an asymmetric synthesis method of the pyrrolidine route (please see route 2), in which chiral units are constructed by sharpless asymmetric epoxidation, c is 1,4-butylene glycol is subjected to reactions in four steps, i.e. desymmetrization, asymmetric epoxidation, ring opening by allyl bromide Grignard reagent and de-asymmetrization, to obtain chiral alcohol, 3-hydroxylpyrrolidine is then obtained by ring closure in two reactions, 3-hydroxyl is converted into amino having an opposite configuration, and finally, a piperidine ring is constructed by reactions in five steps to obtain a compound of formula (I), the process flow of this route has as long as 11 steps, furthermore, the process cost in construction of chiral skeletons by sharpless is relatively high, so there is no value in industrial production.

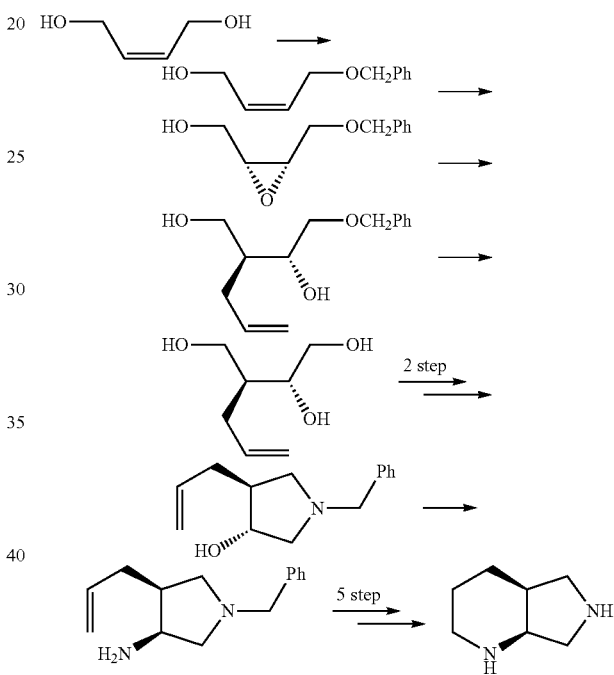

Route 2

Regardless of use of the resolution method or the asymmetric synthesis method for preparation of the compound of formula (I), all the existing synthesis techniques have such defects as high process cost and complex process flow, in addition, the compound is a main intermediate for preparation of moxifloxacin, so development of a synthesis technique with low cost and short process flow will bring enormous market application value.

SUMMARY OF THE INVENTION

An objective of the invention is to overcome the defects in the prior art and provide an asymmetric synthesis method, related raw material and a preparation method of (S,S)-2,8-diazabicyclo[4,3,0]nonane, in order to lower the process cost, shorten the process flow and reduce the emission of wastes, thus, the present invention has tremendous market application value and is suitable for large-scale popularization and application.

Reductive amination of chiral amine and carbonyl compound is a common method for preparing a chiral amino compound. The inventor has found based on plenty of experimental researches that, an enantiomerically pure product, in which C-4 (carbon linked with alkyl substituent) and C-3 (carbon linked with amino) have the same spatial configuration, can be obtained by dehydration reaction of pyrrolidine-3-ketone with alkyl substituent at 4-position and chiral amine to generate an imide or enamine compound, and then reduction of the imide or enamine compound (as shown in Route 3).

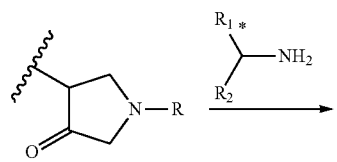

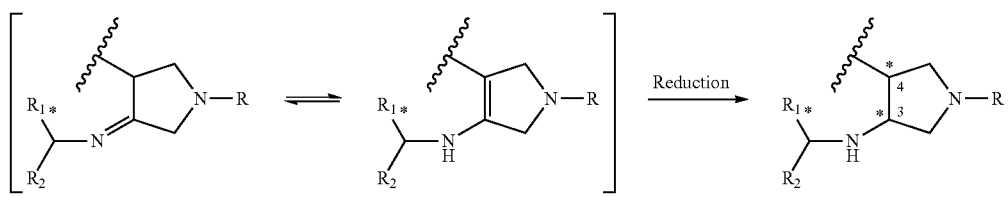

Route 3

Two chiral centers of the target compound (I) can be constructed by selecting the chiral amine with a proper configuration and the pyrrolidine-3-ketone with 4-substituted alkyl for reductive amination, the molecular skeleton of the target compound (I) can be further obtained by selecting a proper functional group on substituted alkyl for cyclization with amino, afterwards, the (S,S)-2,8-diazabicyclo[4,3,0]nonane (I) can be readily obtained by removal of the chiral auxiliary group and amino-protecting group.

The present invention is inexpensive and accessible in selection, a compound of formula (III) or (IV) having the chiral structure of formula (I) is obtained by reductive amination of the conveniently-removed chiral amine(R)-1-phenylethylamine and the pyrrolidine-3-ketone as shown in formula (II), namely, an imide or enamine compound is obtained by dehydration reaction of the pyrrolidine-3-ketone (II) and chiral amine(R)-1-phenylethylamine, and then by reduction of the imide or enamine compound, and this method constitutes the key asymmetric synthesis steps of preparing the (S,S)-2,8-diazabicyclo[4,3,0]nonane (I) in the present invention.

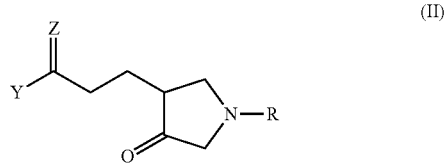

(II)

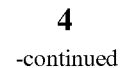

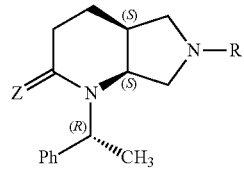

(III)

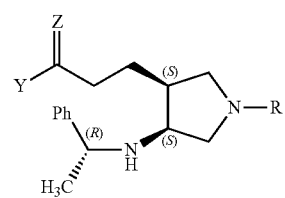

(IV)

wherein, R is an amino-protecting group, especially $C_{1-4}$ alkoxycarbonyl, benzyloxycarbonyl or benzyl which can be removed by hydrolysis or hydrogenation;

Z=$H_2$ or O; when Z=$H_2$, Y is chlorine, bromine, iodine, methanesulfonate, tosylate, hydroxyl or hydroxyl with protection; and when Z=O, Y is $OR_1$, and $R_1$ is $C_{1-4}$ alkyl.

The asymmetric reaction of the pyrrolidine-3-ketone as shown in formula (II) and the chiral amine(R)-1-phenylethylamine comprises the two steps below:

(1) an imide or enamine compound is obtained by dehydration reaction of the pyrrolidine-3-ketone (II) and the chiral amine(R)-1-phenylethylamine (2) reduction of the imide or enamine compound is carried out to obtain the compound of formula (III) or (IV) having the chiral structure of formula (I).

In the step (1), the dehydration method for the pyrrolidine-3-ketone and the chiral amine(R)-1-phenylethylamine is that, a dehydrating agent is added to a proper solvent for dehydration, e.g. molecular sieve, anhydrous calcium chloride and anhydrous magnesium sulfate, and the solvent is methanol, ethanol, n-propanol, isopropanol or a mixed solvent of these alcohols.

Preferably, the dehydration reaction comprises heating reflux in a proper solvent under acidic catalysis, e.g. methanoic acid, acetic acid, trifluoroacetic acid, methanesulfonic acid, paratoluenesulfonic acid, anhydrous hydrogen chloride and the like, and the solvent is methanol, ethanol, n-propanol, isopropanol or a mixed solvent of these alcohols.

More preferably, refluxing water separation is carried out in a proper solvent, the solvent is selected from solvents that can form azeotropy together with water, including benzene, methylbenzene, n-hexane and the like, addition of the catalyst amount of acid can accelerate the dehydration reaction, e.g. methanesulfonic acid and paratoluenesulfonic acid.

The dehydration product of the dehydration reaction is an imide or enamine compound and is directly used for reductive reaction in the next step with no need of separation.

In the step (2), the dehydration product imide or enamine is reduced under different conditions, the resultant reduction product is in cis-configuration, and a compound of formula (III) or (IV) having the chiral structure of formula (I) can be obtained because balance of the enamine and the imide and spatial steric hindrace induction of the chiral auxiliary group are present in the process of reduction at the same time.

The methods for reduction of the dehydration product, i.e. imide or enamine, include catalytic hydrogenation, metal hydride reduction and the like, preferably the catalytic hydrogenation method. The catalyst used in catalytic hydrogenation is selected from nickel or a palladium catalyst, the palladium catalyst is preferably Raney nickel and comprises Pd/C, Pd(OH)$_2$/C, Pd/Al$_2$O$_3$, preferably 10% of Pd/C. Catalytic hydrogenation is carried out in a proper solvent, including tetrahydrofuran, lower aliphatic alcohols such as methanol, ethanol, n-propanol, isopropanol or mixtures of these solvents, and the hydrogenation pressure ranges from normal pressure to 50 MPa.

The compound of formula (III) or (IV) having the chiral structure of formula (I) is obtained by the above asymmetric synthesis steps and has a higher diastereomeric purity from 90% de to 95% de, afterwards, (S,S)-2,8-diazabicyclo[4,3,0]nonane (I) having an entiomeric purity from 90% ee to 95% ee can be obtained by the steps that functional groups Y and Z on substituted alkyl are directly reacted with amino so as to achieve intramolecular cyclization or functional groups Y and Z on substituted alkyl are further converted into active groups capable of reaction with amino so as to achieve intramolecular cyclization, and that the chiral auxiliary group and the amino-protecting group are removed.

When Z=H$_2$ and Y is an active group capable of alkylation reaction with amino, the reductive amination product of pyrrolidine-3-ketone as shown in formula (IIa) is a compound of formula (IIIa) or formula (IVa),

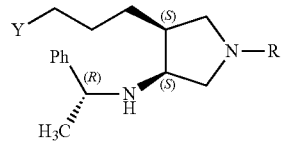
(IIa)

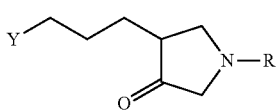
(IIIa)

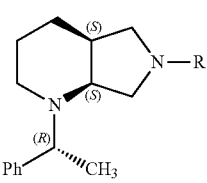

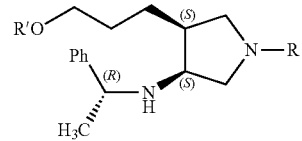
(IVa)

wherein, R is an amino-protecting group, especially C$_{1-4}$ alkoxycarbonyl, benzyloxycarbonyl or benzyl which can be removed by hydrolysis or hydrogenation, and Y is chlorine, bromine, iodine, hydroxyl, methanesulfonate or tosylate.

The active groups in formula (IVa) can be subjected to alkylation reaction with amino under the reductive amination conditions at the same time, so as to obtain partial or total intramolecular cyclization products, and the reductive amination product is a compound of formula (IIIa) or a mixture of formula (IIIa) and formula (IVa).

When Z=H$_2$ and Y is hydroxyl with a protecting group, e.g. C$_{1-4}$ alkanoyl, benzoyl, benzyl, C$_{1-4}$alkyl silicon and the like, the reductive amination product is a compound of formula (IVa'), the hydroxyl-protecting group is then removed and converted into an active group capable of alkylation reaction with amino, e.g. methanesulfonate, tosylate or chlorine, bromine and iodine, afterwards, intramolecular cyclization is carried out to obtain the compound of formula (Ina). In the process of converting hydroxyl with the protecting group in formula (IVa') into the active group, intramolecular cyclization also occurs at the same time to obtain the mixture of formula (IIIa) and formula (IVa).

(IVa')

wherein, R is an amino-protecting group, especially C$_{1-4}$ alkoxycarbonyl, benzyloxycarbonyl or benzyl which can be removed by hydrolysis or hydrogenation, and R' is a hydroxyl-protecting group.

The reductive amination product, which is the mixture of formula (IIIa) and formula (IVa), is continuously and totally converted into the compound of formula (IIIa) without separation in general, for example, by appropriate increase of the reaction temperature, or addition of acidic catalyst to promote complete cyclization.

When Z and Y in pyrrolidine-3-ketone as shown in formula (II) are O and C$_{1-4}$ alkoxyl respectively, the reductive amination product is as shown in formula (IVb), and the intramolecular cyclization product obtained from reaction of functional group carboxylic ester and amino is as shown in formula (IIIb),

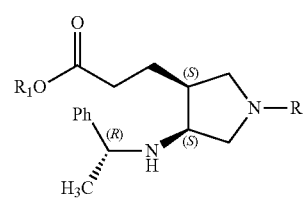
(IVb)

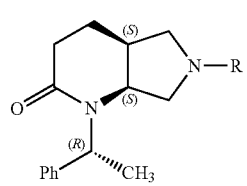
(IIIb)

wherein, R is an amino-protecting group, especially $C_{1-4}$ alkoxycarbonyl, benzyloxycarbonyl or benzyl which can be removed by hydrolysis or hydrogenation, and $R_1$ is a $C_{1-4}$ alkyl.

The compound of formula (IIIb) is further converted into the compound of formula (IIIa) by amide reduction, and the compound of formula (IVb) can also be reduced into hydroxyl at first and then converted into the compound of (IVa), and finally subjected to intramolecular cyclization to obtain the compound of formula (Ma). There are known methods for reduction of amide of formula (IIIb) and carboxylic ester of formula (IVb), e.g. reduction by borane or metal hydrides, the metal hybrids include $NaBH_4$, $LiBH_4$, $KBH_4$, $NaBH_3(CN)$ or $NaBH(OAc)_3$, or metal aluminum hydrides, such as lithium aluminum hydride, bis(methoxyethoxy) aluminum sodium hydride, diisobutyl aluminum hydride and the like.

(S,S)-2,8-diazabicyclo[4,3,0]nonane (I) is obtained by intramolecular cyclization of the compound of formula (IVb) to obtain the compound of formula (Mb) at first, and then amide reduction and removal of the chiral auxiliary group and the amino-protecting group.

Preferably, (S,S)-2,8-diazabicyclo[4,3,0]nonane (I) is obtained by removal of the hydroxyl-protecting group and then intramolecular cyclization of the compound of formula (IVa'), and then removal of the chiral auxiliary group and the amino-protecting group, or is obtained by amide reduction and then intramolecular cyclization of the compound of formula (IVb), and then removal of the chiral auxiliary group and the amino-protecting group.

More preferably, (S,S)-2,8-diazabicyclo[4,3,0]nonane (I) is obtained by reductive amination of the compound of formula (IIa) and chiral amine(R)-1-phenylethylamine to obtain the mixture of formula (IIIa) and formula (IVa), complete conversion of the mixture into the compound of formula (IIIa) without separation, and then removal of the chiral auxiliary group and the amino-protecting group.

The aforementioned amino-protecting group is removed in accordance with known methods. The chiral auxiliary group is removed by a catalytic hydrogenolysis method, and when the amino-protecting group is benzyloxycarbonyl or benzyl, the chiral auxiliary group and the amino-protecting group can be removed in one step by the catalytic hydrogenolysis method. The catalyst incatalytic hydrogenolysis is selected from palladium catalysts, including Pd/C and $Pd(OH)_2C$, the hydrogenation pressure ranges from normal pressure to 10 MPa, in addition, at the presence of acid, e.g. formic acid, acetic acid, trifluoroacetic acid, hydrochloric acid or sulfuric acid, catalytic hydrogenolysis reaction can be accelerated, and the reaction substrate can also be salified and then subjected to catalytic hydrogenolysis reaction.

The novel compounds in the invention are as shown in formula (II), formula (III) and formula (IV) respectively,

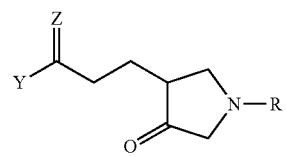
(II)

wherein, R is an amino-protecting group, especially $C_{1-4}$ alkoxycarbonyl, benzyloxycarbonyl or benzyl which can be removed by hydrolysis or hydrogenation. $Z=H_2$ or O; when $Z=H_2$, Y is chlorine, bromine, iodine, methanesulfonate, tosylate, hydroxyl or hydroxyl with protection; and when $Z=O$, Y is $OR_1$, and $R_1$ is $C_{1-4}$ alkyl.

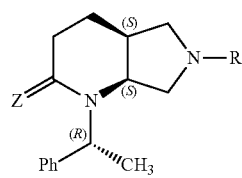
(III)

wherein, R is an amino-protecting group, especially $C_{1-4}$ alkoxycarbonyl, benzyloxycarbonyl or benzyl which can be removed by hydrolysis or hydrogenation. $Z=H_2$ or O.

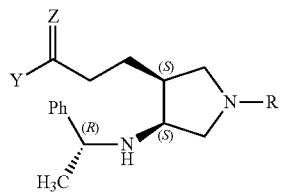
(IV)

wherein, R is an amino-protecting group, especially $C_{1-4}$ alkoxycarbonyl, benzyloxycarbonyl or benzyl which can be removed by hydrolysis or hydrogenation. $Z=H_2$ or O; when $Z=H_2$, Y is chlorine, bromine, iodine, methanesulfonate, tosylate, hydroxyl or hydroxyl with protection; and when $Z=O$, Y is $OR_1$, and $R_1$ is $C_{1-4}$ alkyl.

The invention further relates to a method for preparing the pyrrolidine-3-ketone as shown in formula (II), which is characterized in that, the pyrrolidine-3-ketone as shown in formula (II) is prepared by removal of the carboxylic ester-$COOR_2$ from the compound of formula (V),

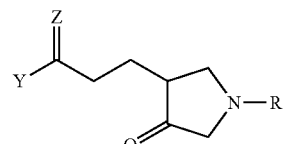
(II)

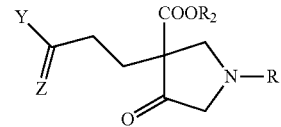
(V)

wherein, R is an amino-protecting group, Z=H$_2$ or O; when Z=H$_2$, Y is chlorine, bromine, iodine, methanesulfonate, tosylate, hydroxyl or hydroxyl with protection; and when Z=O, Y is OR$_1$, and R$_1$ and R$_2$, independent of each other, are C$_{1-4}$ alkyl respectively.

The compound of formula (V) is subjected to hydrolysis reaction of ester in acidic aqueous solution or a basic aqueous solution, and the resultant β-acid ketone is subjected to decarboxylation under heating to obtain the compound of formula (II). When the compound of formula (V) contains other groups that are liable to hydrolysis, other decarboxylation methods can be chosen, e.g. methods described in synthesis, 805 (1982), synthesis, 893 (1982), and removal is carried out by reflux reaction in an apolar aprotic solvent, e.g. DMSO, under the catalysis of a base metal chloride, e.g. sodium chloride. When a hydrolysis decarboxylation method is chosen, the decarboxylation reaction further comprises the procedures of re-esterification (Y and Z are ester groups) and reproduction of the amino-protecting group or conversion thereof into other protective groups (R is oxycarbonyl or acyl that is liable to hydrolysis).

A compound of formula (Va) is prepared by reaction of the compound of formula (VI) and the compound of formula (VII) under base catalysis,

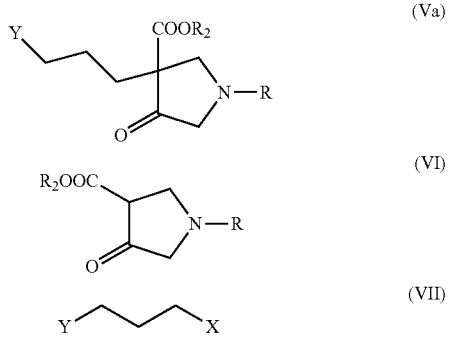

wherein, R is an amino-protecting group, X is chlorine, bromine, iodine, methanesulfonate or tosylate, Y is chlorine, bromine, iodine, methanesulfonate, tosylate, hydroxyl or hydroxyl with protection; and R$_2$ is C$_{1-4}$ alkyl.

The base is sodium alcoholate, sodium hydride, triethylamine, DBU, sodium hydroxide, potassium hydroxide, sodium carbonate or potassium carbonate of C$_{1-4}$.

The compound of formula (Vb) is prepared by conjugate addition reaction of the compound of formula (VI) and the compound of formula (VIII),

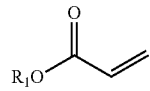

wherein, R is an amino-protecting group, and R$_1$ and R$_2$, independent of each other, are C$_{1-4}$ alkyl respectively.

The conjugate addition reaction (also known as Michael addition) of the compound of formula (VI) and the compound of formula (VIII) is carried out under base catalysis, the base is sodium alcoholate, sodium hydride, triethylamine, DBU or LDA of C$_{1-4}$, and the conjugate addition reaction can also be carried out through free radical reaction under the catalysis of triphenylphosphine.

The compound of 4-alkoxycarbonyl-3-pyrrolidone (VI) is a starting material that is inexpensive and easily available, and can be prepared using known methods (J Org Chem, (1965), 740-744).

In the invention, the compound of pyrrolidine-3-ketone (II) is prepared from an inexpensive and easily available raw material, and (S,S)-2,8-diazabicyclo[4,3,0]nonane having an entiomeric purity from 90% ee to 95% ee is obtained by such simple steps as reductive amination of the compound with chiral amine(R)-1-phenylethylamine, intramolecular cyclization and removal of the auxiliary group, thus, the method of the invention has low process cost is low, short process flow, tremendous market application value and great suitability for large-scale popularization and application.

DETAILED DESCRIPTION OF THE PREFERRED EMBODIMENT

Embodiment 1 Preparation of (S,S)-2,8-diazabicyclo[4,3,0]nonane

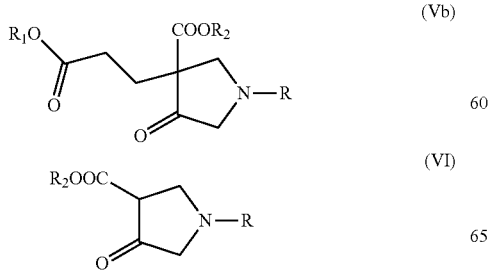

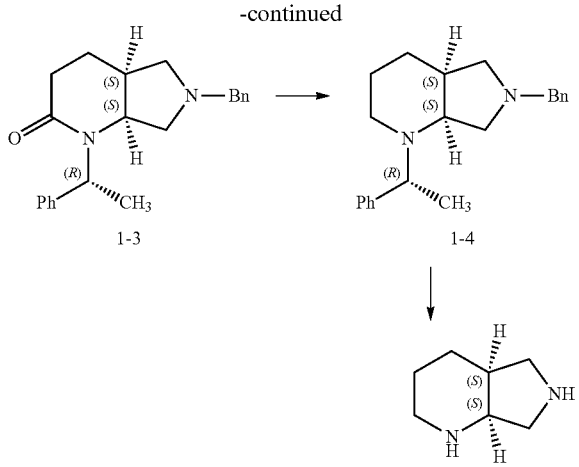

1-benzyl-4-(3-ethoxycarbonyl propyl)-3-pyrrolidone (1-1, 17.0 g, 62 mmol), (R)-1-phenethylamine (7.87 g, 65 mmol) and 150 ml benzene are subjected to refluxing water separation reaction for 6 h under the protection of nitrogen. At the end of the reaction, the solvent is dried by concentration under reduced pressure, the resultant oily product is dissolved in 100 ml anhydrous ethanol and then added to an autoclave, 10 g Raney nickel is added to the autoclave for the purpose of hydrogenation reaction for 72 hours at room temperature under a pressure of 1.0 MPa. Filtration is carried out upon complete reaction, the filtrate is dried by concentration under reduced pressure to obtain 20 g oily product, which is then subjected to column chromatographic separation to obtain 13.5 g oily product (1-2), and the yield is 57%. $^1$H NMR (500 MHZ, CDCl$_3$) δ7.34-7.23 (m, 10H), 4.16-4.12 (m, 2H), 3.76-3.75 (m, 1H), 3.54 (q, J=13.0 Hz, 2H), 3.23-3.22 (m, 1H), 2.81-2.72 (m, 2H), 2.34 (t, J=7.75, 2H), 2.21-2.18 (m, 3H), 1.94 (m, 1H), 1.31-1.25 (m, 7H). MS-ESI: m/z: 381 (M$^+$+1).

The reductive amination product (1-2, 10.8 g, 28.3 mmol) in the previous step, 220 ml toluene and 42 ml acetic acid are heated up to 70° C. and then reacted for 16 h. Upon complete reaction, the reactant is washed by sodium bicarbonate aqueous solution until the pH is about 8, aqueous phase is combined, extraction is carried out by 60 ml toluene, toluene phase is combined, washed with water and dried by anhydrous sodium sulfate, the solvent is dried by concentration under reduced pressure to obtain 9.0 g oily product (1-3), and the yield is 95%. HNMR (500 MHZ, CDCl$_3$) δ7.35-7.24 (m, 10H), 6.03 (q, J=7.1 Hz, 1H), 3.65-3.61 (m, 2H), 3.47 (d, J=12.9 Hz, 1H), 3.07 (t, J=8.3 Hz, 1H), 2.87 (t, J=8.3 Hz, 1H), 2.54-2.19 (m, 5H), 1.67-1.66 (m, 2H), 1.48 (d, J=7.2 Hz, 3H). MS-ESI: m/z: 335 (M$^+$+1).

9.0 g lithium aluminum hydride is added to 20 ml anhydrous tetrahydrofuran, the product (1-9 g, 27 mmol) is slowly dripped in to 25 ml tetrahydrofuran solution under the protection of nitrogen, the temperature is maintained within a range from −10° C. to −15° C., this dripping is followed by heating reflux for 3 hours, the temperature is lowered to 0° C. upon complete reaction, saturated ammonium chloride aqueous solution is dripped for the purpose of reaction quenching, extraction is carried out by ethyl acetate (50 ml×3 times) and is followed by water washing, drying by anhydrous sodium sulfate and filtration, the filtrate is dried by concentration under reduced pressure to obtain oily product, which is then subjected to column chromatographic separation to obtain 5.3 g oily product (1-4), and the yield is 62%. $^1$HNMR (500 MHZ, CDCl$_3$) δ7.38-7.20 (m, 10H), 3.73 (q, J=13.5 Hz, 2H), 3.63-3.58 (m, 2H), 2.86-2.72 (m, 3H), 2.57 (t, J=4.5 Hz, 1H), 2.29-2.26 (m, 3H), 1.61-1.60 (m, 4H), 1.30 (d, J=6.5 Hz, 3H). MS-ESI: m/z: 321 (M$^+$+1).

The product (1-4, 5.3 g, mmol) is dissolved in 100 ml methanol, HCl/methanol solution is added to adjust the pH to be equal to 1.0, 1.0 g activated carbon is added and then stirred for 0.5 h, and the activated carbon is removed by filtration. The filtrate is added with 0.5 g 10% Pd/c, introduced with hydrogen to obtain a pressure of 1.5 MPa and reacted overnight at room temperature, Pd/c is removed by filtration upon complete reaction, and washing is carried out by 5 ml methanol. The filtrates are combined and then the pH is adjusted to be equal to 10.0 by sodium methylate/methanol solution, salts are removed by filtration, and (S,S)-2,8-diazabicyclo[4,3,0]nonane (1.52 g, yield 73%, 95.0% ee) is obtained by distillation under reduced pressure after mother liquor is dried by concentration. $^1$H NMR (500 MHZ, CDCl$_3$) δ3.08-3.07 (m, 1H), 3.06-2.81 (m, 4H), 2.70-2.67 (m, 1H), 2.52-2.51 (m, 1H), 2.00-1.99 (m, 1H), 1.95-1.87 (br, 2H), 1.63-1.60 (m, 2H), 1.35-1.32 (m, 2H).

Embodiment 2 Preparation of (S,S)-2,8-diazabicyclo[4,3,0]nonane

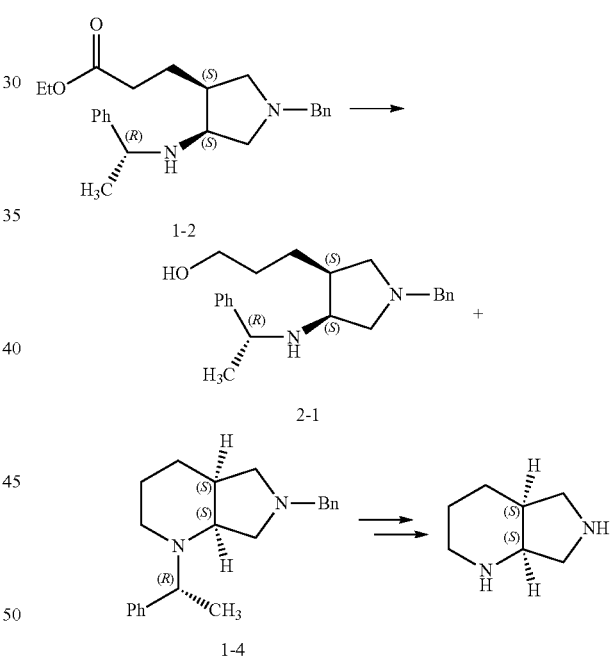

(1-2, 10.0 g, 26.3 mmol), 50.0 ml methanol and 5.8 g sodium borohydride are added to a three-neck falsk, a large amount of bubbles are generated, the temperature rises naturally and reaction is carried out for 3 h. 100.0 ml water is added upon complete spotting plate reaction, and extraction is carried out by 50 ml*2 ethyl acetate. Organic phase is washed with saturated saline solution, dried by anhydrous sodium sulfate and filtered, the filtrate is dried by concentration under reduced pressure to obtain 6.6 g mixture of (2-1) and (1-4), and the product is directly used for the next reaction without classification. A small amount of the mixture is subjected to column chromatography to obtain the product (2-1). $^1$H NMR (500 MHZ, CDCl$_3$) δ7.34-7.24 (m, 10H), 3.80-3.50 (m, 1H), 3.66-3.65 (m, 2H), 3.57-3.52 (m, 2H), 3.39-3.34 (m, 1H), 2.80-2.76 (m, 2H), 2.30-2.27 (m, 1H), 2.23-2.17 (m, 2H), 1.72-1.64 (m, 2H), 1.52-1.45 (m, 1H), 1.36-1.34 (m, 4H), MS-ESI: m/z: 339 (M$^+$+1).

5 g mixture obtained in the previous step is added to 50 ml methylene dichloride, triethylamine (3 g, 30 mmol) is added, mixed solution of methylsulfonyl chloride (1.85 g, 16.2 mmol) and 25 ml methylene dichloride is dripped under ice bath, this dripping is finished 30 minutes later, and reaction is continuously kept for 2 hours at room temperature. 50 ml water is added at the end of reaction, organic phase is separated out and then aqueous phase is extracted by 100 ml methylene dichloride one more time, organic phase is combined, washed with saturated saline solution twice and dried by anhydrous sodium sulfate, and the solvent is dried by spinning to obtain 4.5 g pale yellow viscous liquid (1-4).

The resultant product (1-4) is subjected to deprotection in accordance with the method in the embodiment 1 to obtain (S,S)-2,8-diazabicyclo[4,3,0]nonane, 94.3% ee.

Embodiment 3 Preparation of (S,S)-2,8-diazabicyclo[4,3,0]nonane

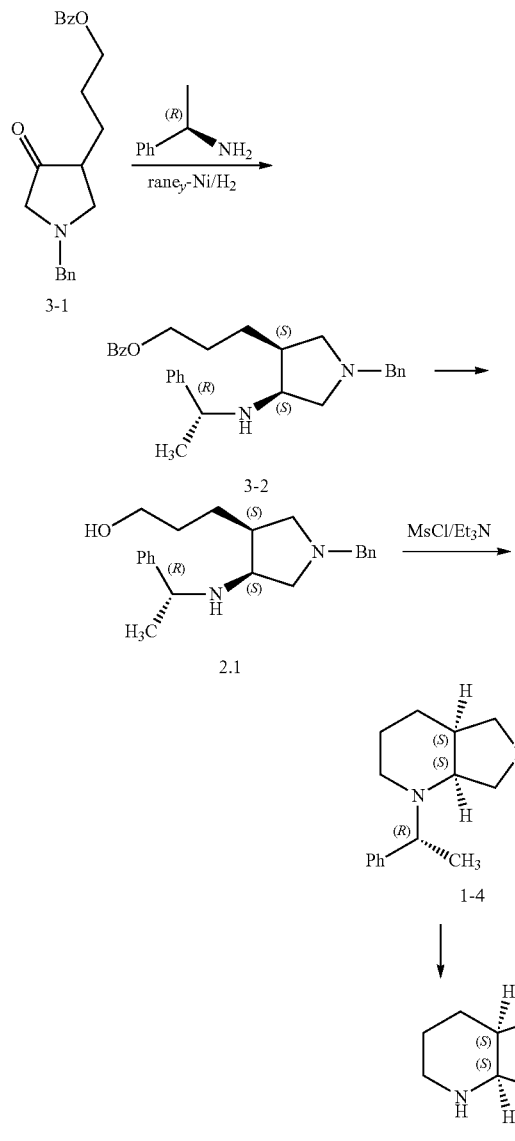

20 ml toluene, 1-benzyl-4-(3-ethoxycarbonyl propyl)-3-pyrrolidone (2.0 g, 5.92 mmol) and (R)-1-phenethylamine (1.0 g, 8.89 mmol) are added to a three-neck flash equipped with a water separator and then subjected to refluxing water separation for 20 hours under the protection of nitrogen, the solvent is dried by spinning in vacuum, the resultant oily product is dissolved in 20 ml ethanol and added to an autoclave, and 0.2 g RaneyNi is added to the autoclave for the purpose of hydrogenation reaction for 24 hours at room temperature under 10 kg pressure. At the end of reaction, the reactant is filtered by a Buchner funnel with diatomite as cushion, and the filtrate is dried by spinning to obtain oily crude product, which is then subjected to column chromatographic separation to obtain oily product (3-2, 3.61 mmol, yield 61.0%). $^1$H NMR (400 MHz, CDCl$_3$) δ 8.06 (d, J=7.6 Hz, 2H), 7.55 (t, J=7.3 Hz, 1H), 7.44 (t, J=7.5 Hz, 2H), 7.20 (m, 10H), 4.36 (t, J=6.0 Hz, 2H), 3.73 (d, J=6.5 Hz, 1H), 3.55 (q, J=12.9 Hz, 2H), 3.24 (d, J=6.3 Hz, 1H), 2.84 (s, 1H), 2.79-2.68 (m, 1H), 2.22 (m, 3H), 1.85-1.69 (m, 3H), 1.44 (m, 1H), 1.28 (m, 4H).

The compound 3-2 (1.4 g, 3.16 mmol) is added to 10 ml methanol, and 1 ml 6N sodium hydroxide aqueous solution is dripped for reaction for 5 hours at room temperature. 20 ml water and 20 ml ethyl acetate are added to the reaction system at the end of reaction, and after layering, aqueous phase is extracted by 20 ml ethyl acetate once, organic phase is combined, washed with saturated saline water twice and dried by anhydrous sodium sulfate, the solvent is dried by spinning to obtain 1.0 g yellow viscous liquid (2-1), and the product can be directly used in the next step with no need of purification.

The oily product (2-1, 1.0 g, 2.95 mmol) obtained in the previous step is added to 10 ml methylene dichloride, triethylamine (0.59 g, 5.90 mmol) is added, the temperature is lowered to 10° C., mixed solution of methylsulfonyl chloride (0.37 g, 3.24 mmol) and 5 ml methylene dichloride is dripped under the protection of nitrogen, this dripping is finished 30 minutes later, and reaction is continued for 2 hours while the temperature is kept at 10° C. 10 ml water is added at the end of reaction, organic phase is separated out and then aqueous phase is extracted by 20 ml methylene dichloride once, organic phase is combined, washed with saturated saline solution twice and dried by anhydrous sodium sulfate, the solvent is dried by spinning to obtain 0.86 g pale yellow viscous liquid (1-4), and the yield of these two steps is 85%.

The resultant product (1-4) is subjected to deprotection in accordance with the method in the embodiment 1 to obtain (S,S)-2,8-diazabicyclo[4,3,0]nonane, 95.3% ee.

Embodiment 4 Preparation of (S,S)-2,8-diazabicyclo[4,3,0]nonane

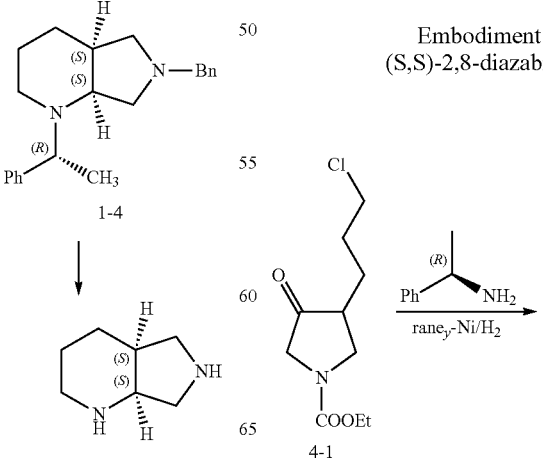

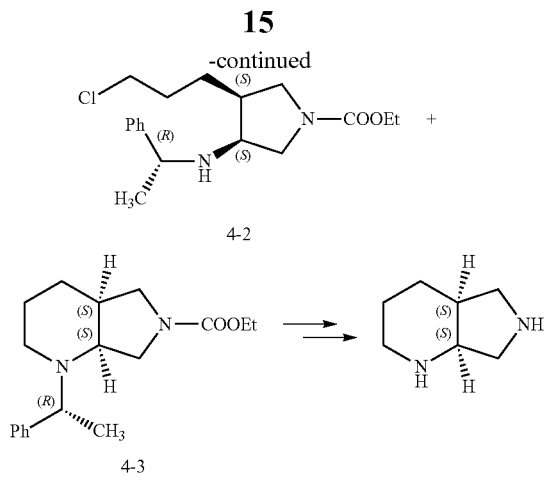

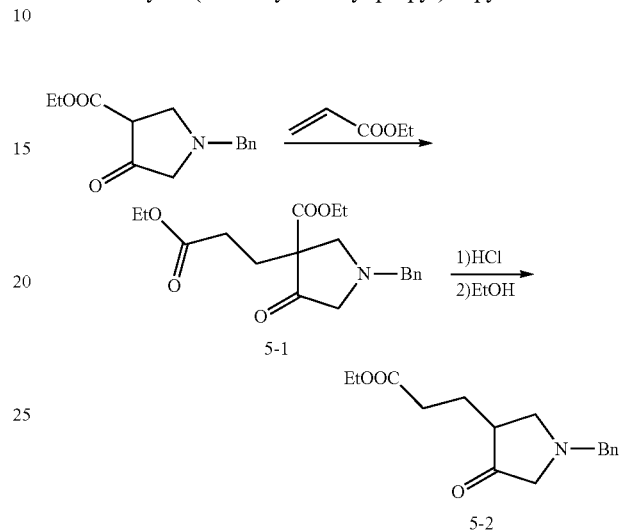

(4-1, 10.0 g), 5.5 g (R)-1-phenethylamine and 100 ml cyclohexane are added to a 250 ml single-neck flask with a reflux dehydration device and then stirred, heated up and dehydrated by refluxing under the protection of nitrogen so as to carry out reaction for 5 hours. The reaction is complete according to HPLC monitoring, the temperature is lowered, and cyclohexane is dried by concentration under reduced pressure at the temperature below 40° C. to obtain 14.8 g oily product. The oily product is dissolved in 50 ml anhydrous ethanol and then transferred to an autoclave, 7.0 g wet Raney nickel is added, nitrogen is introduced to the autoclave to obtain a pressure of 3.0 MPa after three nitrogen displacements, reaction is carried out for three days at normal temperature, and after complete reaction of the raw materials, the main products are (4-2) and (4-3) according to LC-MS. (4-2) is totally converted into (4-3) according to LC-MS after such steps of filtrating the products, eluting the filtrate by anhydrous ethanol, and heating and refluxing the filtrate for 1.5 hours under the protection of nitrogen, ethanol is subjected to concentration under reduced pressure at the temperature below 40° C. until no liquid is discharged, so as to obtain oily liquid, 200 ml saturated sodium bicarbonate aqueous solution and 150 ml petroleum ether are added to a flask, then stirred for 1 hour at normal temperature and left to stand until layering, aqueous phase is extracted by petroleum ether twoce (80 ml×2), organic phase is combined, washed with 100 ml water three times and dried by anhydrous sodium sulfate, and petroleum ether is dried by concentration at the temperature below 40° C. to obtain 9.0 g oily liquid (4-3). 1H NMR (500 MHZ, CDCl$_3$) δ7.33-7.23m, 5H), 4.17-4.12 (m, 2H), 3.68-3.57 (m, 3H), 3.35-3.32 (m, 2H), 3.27-3.22 (m, 1H), 2.42-2.39 (m, 1H), 2.29-2.25 (m, 2H), 1.62-1.22 (m, 8H).

The product (4-3. 9.0 g) in the previous step, 3.0 g 10% palladium on carbon and 50.0 ml acetic acid are added to an autoclave, hydrogen is introduced to the autoclave to obtain a pressure of 1.0 MPa after three nitrogen displacements, and reaction is carried out for 48 h at room temperature. The reactant is dried by concentration under reduced pressure upon complete reaction, the resultant oily product is added to 50 ml NaOH (10%) solution and heated up for reflux reaction for 24 hours, the reactant is extracted by 100 ml chloroform three times upon complete reaction, and the solvent is dried by concentration and then distilled under reduced pressure to obtain 3.1 g (S,S)-2,8-diazabicyclo[4,3,0]nonane with the total yield of 57%, 94.3% ee.

Embodiment 5 Preparation of 1-benzyl-4-(3-ethoxycarbonyl propyl)-3-pyrrolidone 1-benzyl-4-(3-ethoxycarbonyl propyl)-3-pyrrolidone (5.0 g, 20.2 mmol), ethyl acrylate (6.0 g, 60.0 mmol), triphenylphosphine (0.45 g, 1.7 mmol) and 25 ml acetonitrile are heated for reflux reaction for 20 hours, the solvent is dried by concentration under reduced pressure upon complete reaction, so as to obtain oily liquid, and the oily liquid is subjected to column chromatographic separation to obtain oily product (5-1) (3.7 g, yield 53%). 1HNMR (500 MHZ, CDCl$_3$) δ7.38-7.26 (m, 5H), 4.22-4.09 (m, 4H), 3.76-3.70 (m, 2H), 3.37 (d, J=9.65 Hz, 1H), 3.10 (dd, J=77.5 Hz 17.3 Hz, 2H), 2.76 (d, J=9.65 Hz, 1H), 2.51-2.10 (m, 4H), 1.30-1.22 (m, 6H). MS-ESI: m/z: 348 (M++1).

The product (5-1) (3.0 g, 8.6 mmol) in the previous step and 30 g 6N hydrochloric acid are heated for reflux reaction for 10 hours. After water is dried by concentration under reduced pressure upon complete reaction, 15 ml isopropanol is added and stirred at room temperature until dissolution is achieved, afterwards, the temperature is lowered to 0° C. for the purpose of crystallization, and solids are collected by filtration and then dried under reduced pressure at the temperature of 45° C. to obtain 1.8 g white-like solids. 15 ml anhydrous ethanol is added to dissolve the aforementioned solids, thionyl chloride (0.9 g, 7.5 mmol) thionyl chloride is dripped at the temperature of 0° C., followed by heating and reflux reaction for 3 hours. The solvent is dried by concentration under reduced pressure upon complete reaction, 10 ml ethyl acetate is added, the pH is adjusted to be from 8 to 9 by saturated sodium bicarbonate aqueous solution, aqueous phase is extracted by ethyl acetate (10 ml×twice) after layering, organic phase is combined and dried by anhydrous sodium sulfate, and the solvent is dried by concentration under reduced pressure to obtain oily product (5-2) (1.7 g, yield 72%). $^1$HNMR (500 MHZ, CDCl$_3$) δ7.34-7.26 (m, 5H), 4.11 (q, J=7.15 Hz, 2H), 3.71-3.65 (m, 2H), 3.29-3.23 (m, 2H), 2.74 (d, J=17.3 Hz, 1H), 2.47-2.36 (m, 4H), 2.07-2.04 (m, 1H), 1.72-1.70 (m, 1H), 1.32-1.22 (m, 3H). MS-ESI: m/z: 276 (M$^1$+1).

Embodiment 6 Preparation of 1-ethoxycarbonyl-4-(3-chloropropyl)-3-pyrrolidone

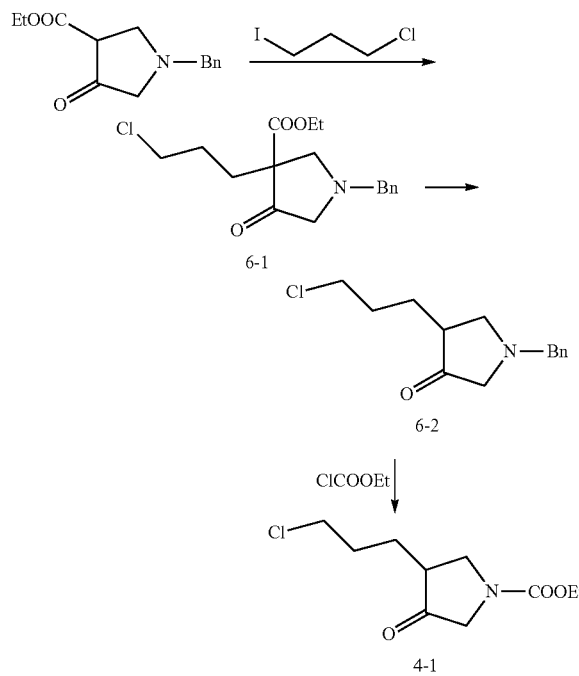

1-benzyl-4-ethoxycarbonyl-3-pyrrolidone (2.5 g, 10.1 mmol) is dissolved in 25 ml tetrahydrofuran and then cooled by ice water bath, triethylamine (2 g, 20.2 mmol) is added and stirring is performed for 30 minutes, 1-chloro-3-iodopropane (4.12 g, 20.2 mmol) is dripped, this dripping is finished 30 minutes later, afterwards, the temperature is raised to room temperature for the purpose of continuous reaction for 18 hours. Extraction is carried out by methylene dichloride (10 ml×3 times) at the end of reaction, organic phase is combined and dried by anhydrous sodium sulfate, and the solvent is dried by concentration under reduced pressure to obtain oily product, which is then purified by column chromatography to obtain oily product (6-1) (2.12 g, 6.57 mmol, yield 65%). $^1$H NMR (500 MHz, CDCl$_3$) δ7.34-7.27 (m, 5H), 4.17 (q, J=7.1 Hz, 2H), 3.71 (s, 2H), 3.48-3.51 (m, 2H), 3.40 (d, J=9.6 Hz, 1H), 3.19 (d, J=17.2 Hz, 1H), 2.99 (d, J=17.2 Hz, 1H), 2.73 (d, J=9.6 Hz, 1H), 2.04-2.02 (m, 1H), 1.92-1.89 (m, 2H), 1.71-1.69 (m, 1H), 1.24 (t, J=7.1 Hz, 3H). MS-ESI: m/z: 324 (M$^+$+1).

The product (6-1, 2.0 g, 6.2 mmol) in the previous step is added to 25 ml 6N hydrochloric acid for the purpose of reflux reaction for 8 hours. Water is dried by concentration under reduced pressure at the end of reaction, 10 ml isopropanol is added, crystallization is carried out for 2 hours at the temperature of 0° C., solids are collected by filtration and then dried under reduced pressure at the temperature of 45° C. to obtain white-like solid product (6-2) (0.91 g, yield: 58%). $^1$H NMR (500 MHz, CDCl$_3$) δ7.36-7.27 (m, 5H), 3.70 (s, 2H), 3.54-3.51 (m, 2H), 3.30 (d, J=8.0 Hz, 1H), 3.25 (d, J=17.0 Hz, 1H), 2.74 (d, J=17.0 Hz, 1H), 2.46-2.44 (m, 2H), 2.37 (dd, J=8.8 Hz, 8.0 Hz, 1H), 1.91-1.86 (m, 2H), 1.86-1.79 (m, 1H), 1.55-1.50 (m, 1H). MS-ESI: m/z: 252 (M$^+$+1).

The product (6-2, 0.9 g) in the previous step, 12 ml saturated sodium bicarbonate solution and 10 ml methylene dichloride are added to a four-neck flask. 2-hour stirring is followed by layering. Water phase is extracted by 10 ml methylene dichloride and then extracted by 10 ml*2 methylene dichloride. Organic phase is combined and is washed by addition of 20 ml*2 saturated saline solution. Organic phase is dried by addition of 0.5 g magnesium sulfate. Black oily product (0.85 g, HPLC purity: 95%) is obtained after filtration and then drying by concentration at the temperature of 35° C. 18 ml ethyl chlorocarbonate is dripped into the aforementioned oily product under ice bath, followed by heating and refluxing (90-95° C.) for 3 hours. The reaction is complete in accordance with HPLC detection, and 0.9 g (4-1) oily product is obtained by drying the reactant by concentration at the temperature of 50-55° C. $^1$H NMR (500 MHz, CDCl$_3$) δ4.21-4.16 (m, 3H), 4.05-3.90 (m, 1H), 3.74-3.70 (m, 1H), 3.56-3.53 (m, 2H), 3.34-3.30 (m, 1H), 2.58-2.42 (m, 1H), 1.95-1.82 (m, 3H), 1.63-1.57 (m, 1H), 1.28-1.25 (m, 3H). MS-ESI: m/z: 234 (M$^+$1).

Embodiment 7 Preparation of 1-benzyl-4-(3-benzyloxy-propyl)-3-pyrrolidone

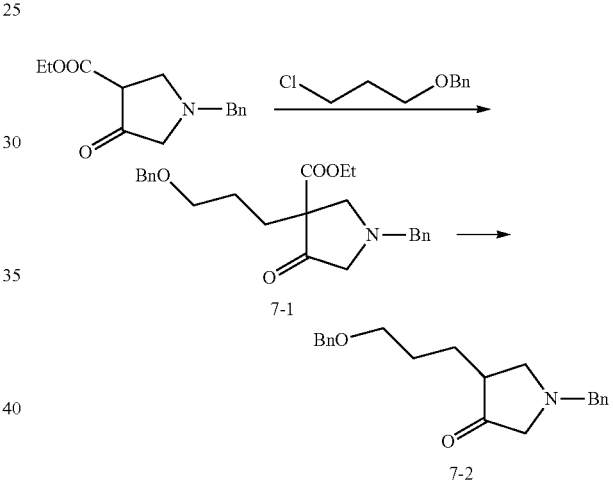

1-benzyl-4-ethoxycarbonyl-3-pyrrolidone (10.0 g, 40.4 mmol), 3-chloropropylbenzylether (11.0 g, 60.6 mmol), potassium iodide (3.3 g, 20.2 mmol), tetrabutylammonium bromide (1.3 g, 4.04 mmol) and DBU (12.0 g, 80.8 mmol) are added to 150 ml ethylene glycol dimethyl ether and then subjected to reflux reaction for 4 hours under the protection of nitrogen. 150 ml water is added at the end of reaction, extraction is carried out by ethyl acetate (100 ml×3 times), organic phase is combined, washed once by saturated saline water and dried by anhydrous sodium sulfate, and the solvent is dried by concentration under reduced pressure to obtain oily product, which is then purified by column chromatography to obtain oily product (7-1) (10.3 g, 26.0 mmol, yield: 64.4%). $^1$H NMR (500 MHz, CDCl$_3$) δ7.33-7.27 (m, 10H), 4.47 (s, 2H), 4.17 (q, 2H), 3.67 (t 2H), 3.46-3.43 (m, 3H), 3.19 (d, J=17.1 Hz, 1H), 2.94 (d, J=17.1 Hz, 1H), 2.72 (d, 1H), 2.04-1.98 (m, 1H), 1.85-1.82 (m, 1H), 1.72-1.71 (m, 1H), 1.56-1.53 (m, 1H), 1.24 (t, 3H).

The product (7-1)(10.3 g, 26.0 mmol) in the previous step is added to 50 ml 6N hydrochloric acid for the purpose of reflux reaction for 5 hours. Water is dried by concentration under reduced pressure at the end of reaction, 30 ml water is added, the pH is adjusted to be within an alkaline range by saturated sodium carbonate aqueous solution, extraction is carried out by ethyl acetate (100 ml×3 times), organic phase is combined, washed once by saturated saline water and dried by anhydrous sodium sulfate, and the solvent is dried by concentration under reduced pressure to obtain oily product, which is then purified by column chromatography to obtain oily product (7-2) (5.7 g, 17.6 mmol, yield: 67.7%).

Embodiment 8 Preparation of 1-benzyl-4-(3-benzoyloxypropyl)-3-pyrrolidone

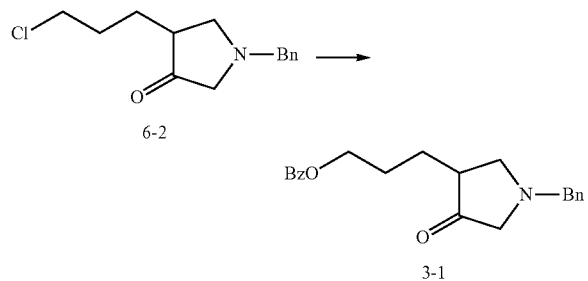

1-benzyl-4-(3-chloropropyl)-3-pyrrolidone hydrochloride (6-2, 5.0 g, 17.3 mmol), benzoic acid (2.5 g, 20.8 mmol), potassium carbonate (7.1 g, 51.9 mmol) and potassium iodide (1.4 g, 8.65 mmol) are added to 40 ml DMF, then heated up to 100° C. and finally reacted overnight. At the end of reaction, the temperature is lowered to room temperature, 100 ml water is added, extraction is carried out by ethyl acetate (100 ml×2), organic phase is combined, washed twice by saturated saline water and dried by anhydrous sodium sulfate, and the solvent is dried by concentration under reduced pressure to obtain oily product, which is then purified by column chromatography to obtain oily product (3-1, 2.4 g, 7.1 mmol, yield: 41.1%). $^1$H NMR (400 MHz, CDCl$_3$) δ 8.03 (d, J=8.1 Hz, 2H), 7.56 (t, J=7.4 Hz, 1H), 7.44 (t, J=7.7 Hz, 2H), 7.38-7.27 (m, 5H), 4.32 (t, J=6.3 Hz, 2H), 3.70 (s, 2H), 3.37-3.21 (m, 2H), 2.76 (d, J=17.2 Hz, 1H), 2.50 (dd, J=13.4, 8.0 Hz, 1H), 2.41 (t, J=8.9 Hz, 1H), 1.98-1.71 (m, 3H), 1.54 (m, 1H).

Embodiment 9 Preparation of (3S,4S)-1-benzyl-3 [(1R)-phenylethylamino]-4-(3-chloropropyl)-pyrrolidine

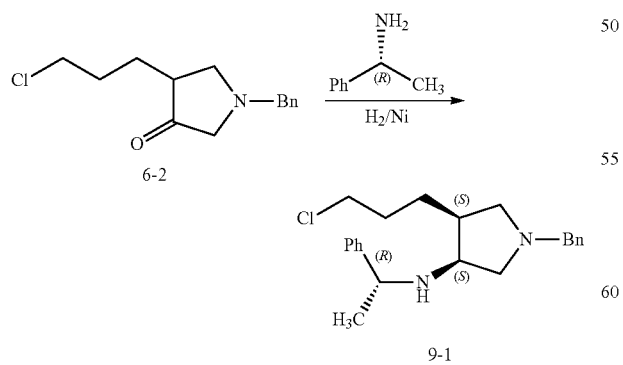

1-benzyl-4-ethoxycarbonyl-3-pyrrolidone (6-2 in the Embodiment 6, 12.0 g, 48 mmol), (R)-1-phenethylamine (6.0 g, 50 mmol) and 150 ml benzene are subjected to refluxing water separation under the protection of nitrogen, and upon complete water separation, the solvent is dried by concentration under reduced pressure to obtain oily product, the oil product is dissolved in 100 g anhydrous ethanol and added to an autoclave, 7 g Raney nickel is added to the autoclave for the purpose of hydrogenation reaction for 60 hours at room temperature under a pressure of 1 MPa. Filtration is carried out upon complete reaction, the filter cake is eluted by ethanol, the filtrate is dried by concentration under reduced pressure to obtain 16 g oily product, which is then subjected to column chromatographic separation to obtain oily product (compound 9-1, 6.2 g, yield 36%). $^1$H NMR (500 MHZ, CDCl$_3$) δ7.34-7.23 (m, 10H), 3.80-3.50 (m, 5H), 3.23-3.22 (m, 1H), 2.81-2.72 (m, 2H), 2.21-2.18 (m, 2H), 1.93 (m, 1H), 1.57-1.25 (m, 7H). MS-ESI: m/z: 357 (M$^+$+1).

We claim:
1. A compound which has a structural formula as shown in formula (IIa),

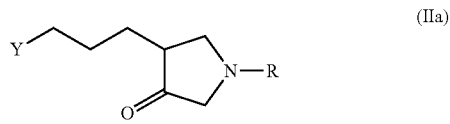

wherein, R is an amino-protecting group selected from the group consisting of $C_{1-4}$ alkoxycarbonyl, benzyloxycarbonyl and benzyl which can be removed by hydrolysis or hydrogenation;
Y is one of chlorine, bromine, iodine, methanesulfonate, tosylate, or hydroxyl.

2. A method for preparing the compound of claim 1 as shown in formula (IIa), where the pyrrolidine-3-ketone as shown in formula (IIa) is prepared by removal of the carboxylic ester-COOR$_2$ from a compound of formula (Va),

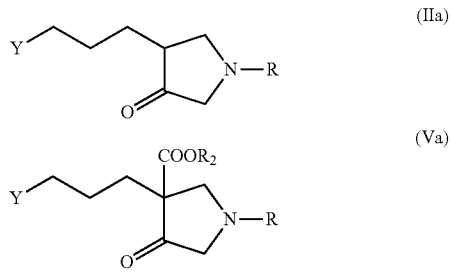

wherein, R is an amino-protecting group, Y is one of chlorine, bromine, iodine, methanesulfonate, tosylate, or hydroxyl and, R$_2$ is $C_{1-4}$ alkyl.

3. The method according to claim 2, where a compound of formula (Va) is prepared by base catalysis of a compound of formula (VI) and a compound of formula (VII),

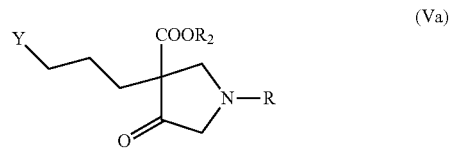

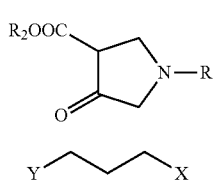
Y∼∼∼X  (VII)
wherein, R is an amino-protecting group, X is one of chlorine, bromine, iodine, methanesulfonate or tosylate, Y is one of chlorine, bromine, iodine, methanesulfonate, tosylate, or hydroxyl; and $R_2$ is $C_{1-4}$ alkyl.
* * * * *